United States Patent [19]
Behnk

[11] Patent Number: 5,993,741
[45] Date of Patent: Nov. 30, 1999

[54] APPARATUS FOR ANALYZING BODY FLUID

[76] Inventor: Holger Behnk, Holitzberg 61, 22417Hamburg, Germany

[21] Appl. No.: 09/015,644

[22] Filed: Jan. 29, 1998

[30] Foreign Application Priority Data

Feb. 10, 1997 [DE] Germany .................. 297 02 276 U

[51] Int. Cl.⁶ .................................................. G01N 21/00
[52] U.S. Cl. ............................... 422/64; 422/63; 422/67; 436/43; 436/47
[58] Field of Search ................... 422/63, 64, 67; 436/43, 45, 47

[56] References Cited

U.S. PATENT DOCUMENTS

| | | | |
|---|---|---|---|
| 3,322,958 | 5/1967 | Heiss | 250/218 |
| 4,808,380 | 2/1989 | Minekane | 422/64 |
| 4,849,176 | 7/1989 | Sakagami | 422/64 |
| 5,424,837 | 6/1995 | Porte et al. | 356/384 |
| 5,501,838 | 3/1996 | Ootani et al. | 422/65 |
| 5,518,693 | 5/1996 | Tomasso et al. | 422/63 |
| 5,582,796 | 12/1996 | Carey et al. | 422/65 |
| 5,637,275 | 6/1997 | Carey et al. | 422/64 |
| 5,653,940 | 8/1997 | Carey et al. | 422/52 |
| 5,827,479 | 10/1998 | Yamazaki et al. | 422/67 |

FOREIGN PATENT DOCUMENTS 0 502 638 A2  9/1992  European Pat. Off. .
0 589 528 A2  3/1994  European Pat. Off. .

OTHER PUBLICATIONS

Patent Abstracts of Japan; European Patent Office; Publication No. 63317773; Dec. 26, 1988.

*Primary Examiner*—Long V. Le
*Attorney, Agent, or Firm*—Alix, Yale & Ristas, LLP

[57] ABSTRACT

The apparatus for analyzing body fluids which are contained in tubes provided with an externally readable identification marking, with positive sample identification at the position at which a quantity of fluid is removed for analysis, it being possible for the tubes to be inserted into a rotatable rotor (1), is distinguished in that at least two rotors (1) can be pushed into the apparatus in a drawer-like manner, it being possible for these rotors to be driven via a laterally arranged gear wheel (9) in each case which engages in the observation slits which are arranged on the circumference of the rotor (1) and through which the identification of the tubes takes place.

12 Claims, 4 Drawing Sheets

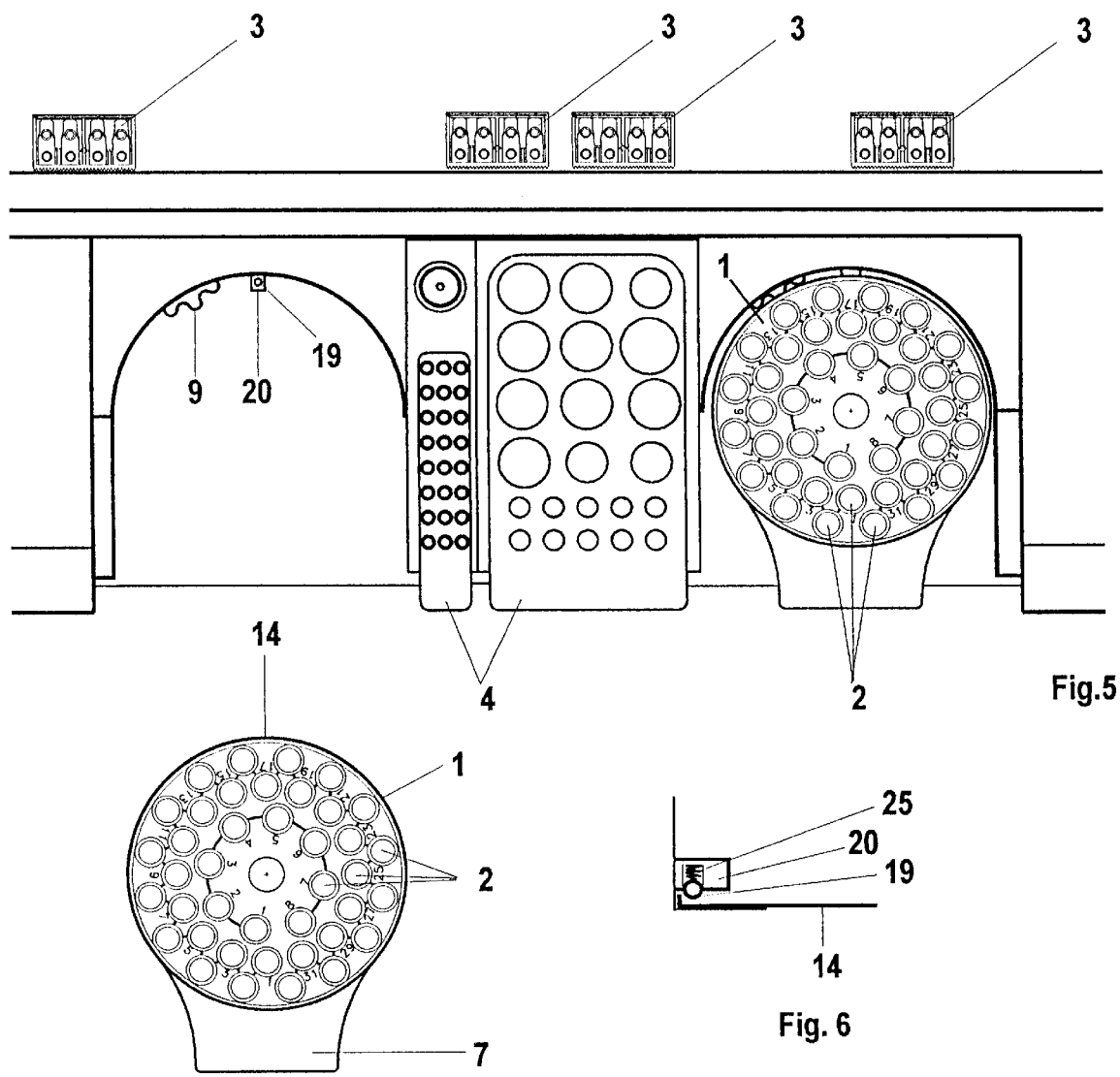

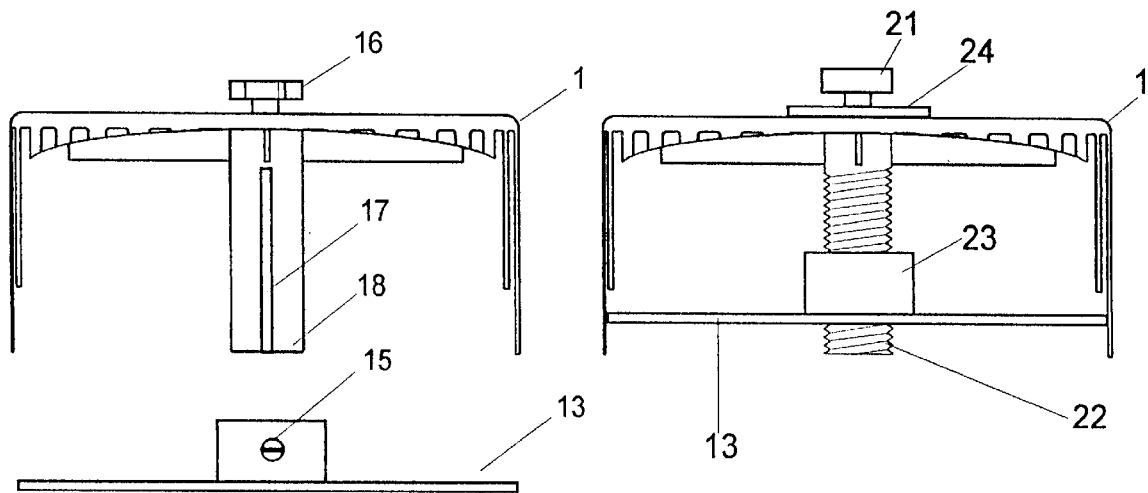
Fig. 7
Fig. 8
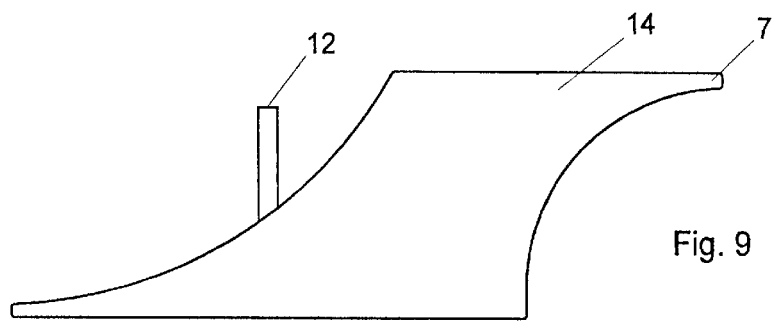
Fig. 9
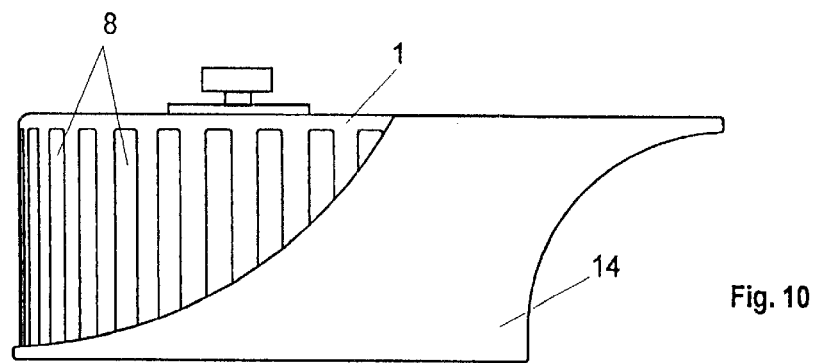
Fig. 10

5,993,741

APPARATUS FOR ANALYZING BODY FLUID

FIELD OF THE INVENTION

The present invention relates to an apparatus for analyzing body fluids which are contained in tubes provided with an externally readable identification marking, with positive sample identification at the position at which a quantity of fluid is removed for analysis, it being possible for the tubes to be inserted into a rotatable rotor.

BACKGROUND OF THE INVENTION

Large quantities of body-fluid samples, in particular blood but also urine and other body fluids, are tested in laboratories. These fluids are contained in sample tubes from which sub-quantities are removed with the aid of pipetting devices in order that one or more analyses can be carried out. This takes place essentially automatically. The main problem here is positive identification. It is, of course, necessary to be sure that the analysis data are assigned to the correct sample, and thus to the correct patient.

For this purpose, it is known for the tubes to be provided with an automatically readable marking, e.g. a bar code. In the case of a previously known apparatus, the tubes are arranged one behind the other in a row in a drawer-like frame and are pushed into the apparatus, the individual markings being identified by an identification device during the push-in operation by virtue of said device reading the bar code. Such a device cannot be 100% reliable since the frames with the tubes may possibly be pushed in incorrectly or it could be possible for a tube to be exchanged after the push-in operation, this exchange not being detected by the apparatus since the identification has already taken place beforehand, namely during the operation for pushing the row of tubes in.

In the case of another apparatus, at the same time as the identification takes place, the fluid from the sample tube is introduced, with the aid of a pipette, into a further tube, which is located in a closed carousel. This ensures positive identification since it is not possible for any sample tubes to be removed from the carousel. The problem which does arise, however, is that two sample tubes have to be used for each body fluid, and this signifies an increase in waste.

It is also known for the tubes to be arranged in the form of a chain and, in this case, for that part of the chain in which the sample removal takes place to be guided through a closed-top chamber such that it is not possible for any tube to be removed. The identification takes place during sample removal by the pipette, thus ensuring positive identification. However, such a chain is complicated, in particular if a number of analyses are to be carried out on the same sample. If the analysis establishes that, due to critical values, a further analysis should be carried out, then the corresponding tube is no longer located at the sample-removal location and so has to be inserted manually again at the beginning of the chain. This is also very complicated.

Finally, it is known for the tubes to be inserted in a carousel or rotor, the identification taking place at the time of sample removal. Although positive identification is ensured, it is necessary, once the measurements have been completed, for the tubes to be removed individually from the rotor or for the rotor, which is positioned on a spindle, to be lifted out in order for the tubes to be disposed of. This is very complicated. There is also the problem of exchange having to take place once the analyses have been completed. If the operator is otherwise occupied at this point, which will usually be the case, then the apparatus remains at a standstill for some time until it is noticed that new tubes have to be inserted. This amount of time wasted means that the apparatus is utilized less economically and it may be necessary for overtime to be worked in order for the day's analyses to be completed as planned.

SUMMARY OF THE INVENTION

The object of the invention is to provide an apparatus in the case of which positive identification is ensured but undesirable unproductive times can be readily avoided and which can be quickly adapted to changed analysis requirements.

The solution according to the invention consists in that at least two rotors can be pushed into the apparatus in a drawer-like manner, it being possible for these rotors to be driven via a laterally arranged gear wheel in each case which engages in the observation slits which are arranged on the circumference of the rotor and through which the identification of the tubes takes place.

It is therefore the case that, rather than there just being one rotor, at least two rotors are provided. Normally, two rotors will also suffice. These rotors do not need to be lifted out laboriously, in which case it is also necessary to release the connection to the drive, which operates from beneath by way of a central spindle. Rather, the rotors can be pushed into the apparatus, and drawn out of it again, in a drawer-like manner. These operations of drawing the rotors out, and pushing them in, from the side, also mean that there is no risk of contact with, or damage to, the pipetting unit, which is arranged above the tubes and the rotors and moves back and forth. The rotors can be driven with the necessary rotary movement by a laterally arranged gear wheel which engages in the observation slits which are arranged on the circumference of the rotor and through which the identification of the tubes takes place. The arrangement is expediently such that, when a rotor is pushed in or drawn out, the gear wheel idles along with it. Said gear wheel thus readily engages with, or disengages from, the observation slits. Since these observation slits have to be provided anyway, there is no need for any additional, high-outlay devices to be provided on the rotor.

The rotors are expediently provided on the circumference with a marking, which can be read by the identification device, for a reference position (zero position).

If a new rotor has been pushed in and the start button has been actuated, then, with the aid of the gear wheel driven by a corresponding motor, in particular a stepping motor, the rotor is rotated until the marking for the reference position (zero position) is detected. From this reference position, advancement then takes place up to the individual observation slits, by virtue of the gear wheel being driven, and, at the slits, the marking is identified and stored. If it is not possible for any marking to be identified at this location, then the rotor is moved back and forth a little with the aid of the stepping motor until the marking is found. Of course, the identification device also establishes if there is no tube at a particular location. At any rate, however, it is thus possible to establish in a precise manner which tube is located at which location of the rotor, with the result that such a tube can be specifically brought into the removal position without all the markings of the tubes having to be read first of all. Identification then takes place during the removal, with the result that it is not possible for any identification errors to occur.

The gear wheels are advantageously provided with a position sensor which senses the individual teeth, with the result that the movement of the gear wheel can be controlled very precisely.

There may be provided in the rotor two rows, arranged in concentric circles, of receiving openings for tubes which can be identified by the identification device. The inner tubes, in this case, are identified by way of the interspace between two outer tubes. Advantageously provided on the inside is a third row for tubes, which is arranged concentrically as a circle and is provided for unplanned tests, e.g. emergency cases. In this row, then, it is possible to insert a tube into a specific location whose position (number) can be input manually into the apparatus, with the result that a measurement can be carried out very quickly here. The identification of this tube is read in by a hand scanner or input manually.

The apparatus expediently has a computer. If such a computer is present, the apparatus may expediently also be connected to an external computer which has data and programs for the analyses which are to be carried out. During the initial sensing of all the sample tubes, the positions of the latter in the rotor are input into the external computer, which can then manage all the analysis operations.

The essential advantage of the apparatus according to the invention, however, is that unproductive times can be readily avoided. If the analyses of the tubes in one rotor have been completed, the apparatus switches over to the other rotor, or a further rotor, which is newly provided with tubes and is on standby. It is then possible at any time during the operation of this new rotor for the old rotor to be removed, the tubes to be exchanged and the rotor to be inserted into the apparatus again. The removable rotor may also serve as a transportation means in order to transport the tubes to the apparatus according to the invention from the location where they are delivered or pretreated, e.g. in a centrifuge.

Tubes come in different lengths. In order for the rotor to be adapted to tubes of a different length, it advantageously has a vertically adjustable base. This vertically adjustable base can expediently be arrested at different heights on a central column by a screw which is accessible through one of the observation slits.

In another embodiment, the vertical adjustment of the base for adaptation to different tube sizes takes place by way of a grip which is fitted at the top of the rotor and is connected to a screw rod which engages in a threaded section in the base. Vertical adjustment of the base can be effected simply by rotating the grip. In this case, the grip may be designed such that it is part of a mount for the insertion of the rotor into a centrifuge.

In order to facilitate the push-in operation and to achieve a reliable, rotation-free operating position in the apparatus, it is expediently provided that the rotors are inserted in mounts which have a flat front side, lateral centring surfaces, which taper to the front, and a grip.

In another embodiment, the mounts are semicircular at the front. Angled securing takes place in this case by way of a recess which interacts with a protrusion which is located on the apparatus and, with correct angled positioning, engages in the recess. Located on this protrusion is a spring-loaded ball which, once the rotor has been inserted correctly, snaps in the recess, with the result that the rotor can be introduced in a simple manner, but is nevertheless retained securely.

It is also possible for a tube to be placed subsequently in an unoccupied location. Then, with a single rotation, the rotor searches for this tube and assigns it. The analyses which are to be carried out are communicated by the external computer or, if there is no such computer present, are input by keyboard.

BRIEF DESCRIPTION OF THE DRAWINGS

The invention is described by way of example hereinbelow using an advantageous embodiment and with reference to the attached drawings, in which:

FIG. 5 shows, in an illustration similar to that in FIG. 1, another embodiment of the apparatus according to the invention;

FIG. 6 shows a detail of the embodiment of FIG. 5;

FIG. 7 shows, in section, an embodiment for the vertical adjustment of the base of the rotor;

FIG. 8 shows, in section, another embodiment for the vertical adjustment of the rotor;

FIG. 9 shows the mount without the rotor inserted; and

FIG. 10 shows the mount with the rotor inserted.

DESCRIPTION OF A PREFERRED EMBODIMENT

Figure 1:
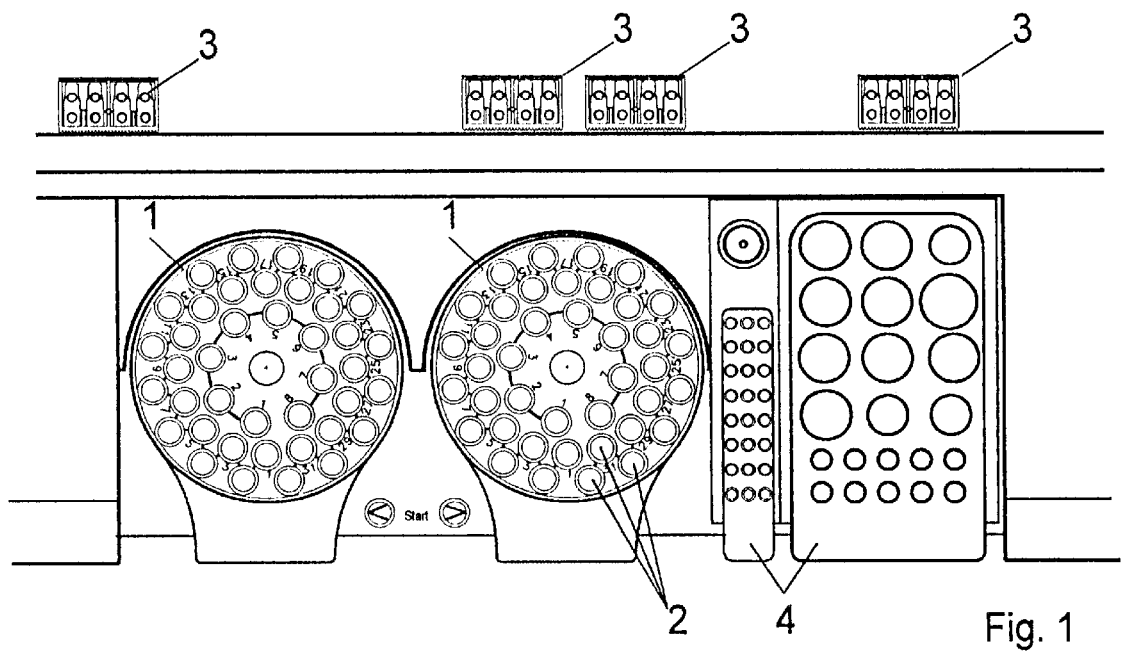
FIG. 1 shows a plan view of one embodiment of the apparatus according to the invention.

FIG. 1 shows the apparatus according to the invention, into which two rotors 1 have been inserted. Tubes (not shown) with the body fluid which is to be tested are located in receiving openings 2 in said rotors. A pipetting device is used to remove from a tube, which is identified at the same time, a certain quantity of body fluid and to introduce this into a cuvette 3. In addition, one or more reagents are removed from a unit 4 by a pipette and introduced into the cuvette 3. This cuvette is then transported on to a testing station.

The rotors 1 can be pushed into the apparatus. A rotor with new tubes can be pushed into the apparatus while this apparatus is still processing the tubes of the other rotor. The start button for the appropriate rotor 1 is then pressed in order that, once processing of the tubes of one rotor has been completed, the apparatus can continue with the processing of the tubes of the other rotor.

Figure 2:
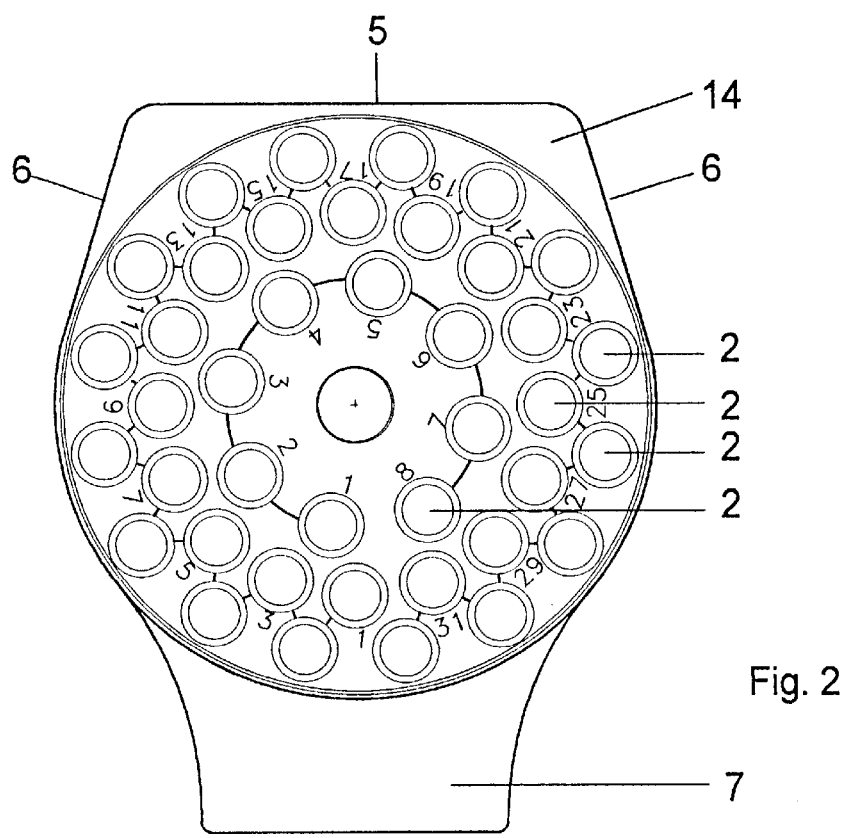
FIG. 2 shows a plan view of a rotor with mount.
Figure 3:
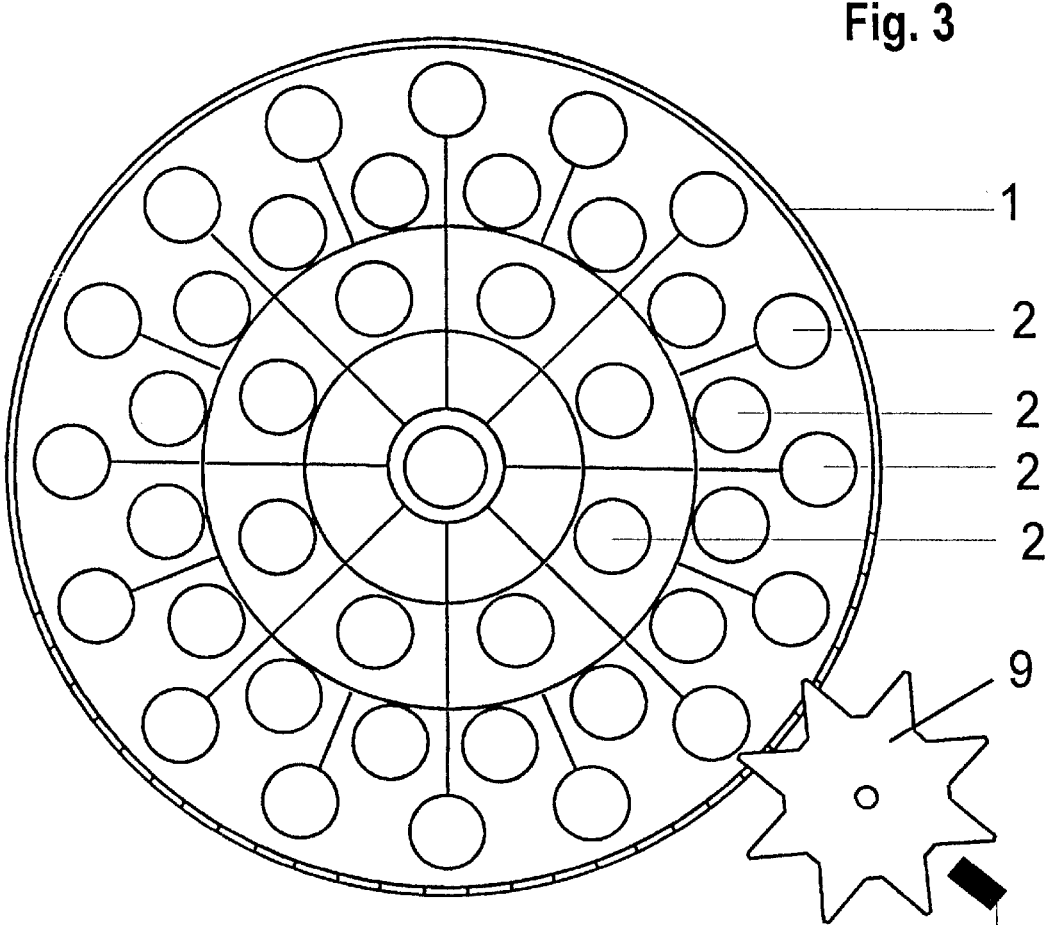
FIG. 3 shows, in a schematic illustration from beneath, the drive for the rotor.
Figure 4:
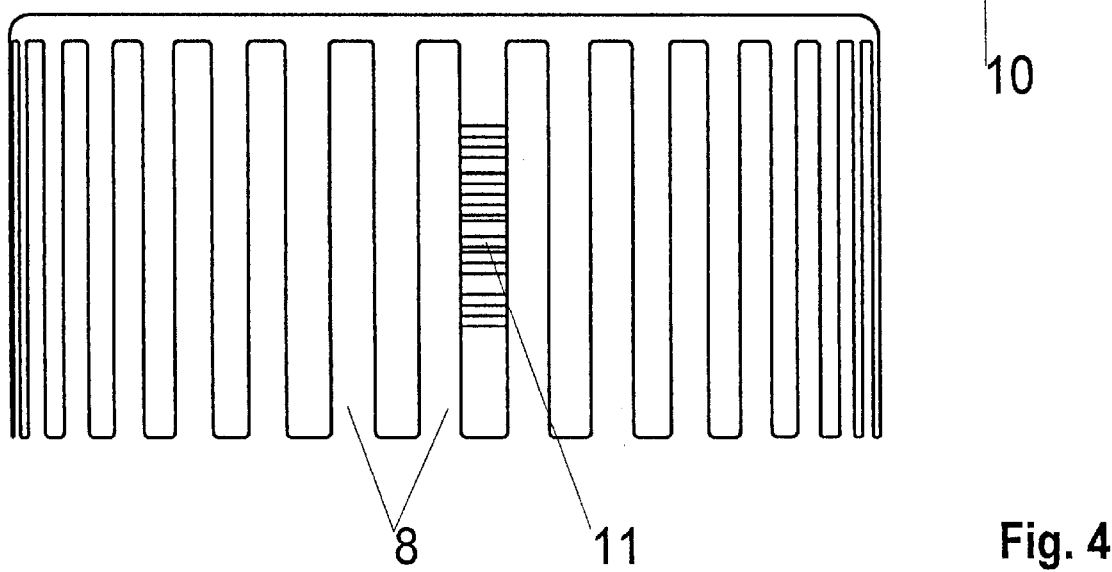
FIG. 4 shows a lateral view of the rotor.

The rotor 1 is shown from above in FIG. 2. It is arranged in a mount 14 which has a planar stop surface 5 at the front, lateral oblique surfaces 6 for centring purposes and a grip 7 at the rear. The receiving openings 2 for the tubes are numbered and arranged in three concentric rows. For the two outer rows, automatic identification can take place through lateral observation slits 8, which are shown, for example, in FIG. 4. These observation slits 8 also assist the rotation of the rotor 1 with the aid of a gear wheel 9, shown in FIG. 3, which is connected to a motor, in particular a stepping motor, and, as the rotor is pushed in or drawn out, idles with the rotor, with the result that it can engage with an observation slit 8.

Located beside the gear wheel is a position sensor 10, which senses the teeth of the gear wheel.

As has been said, identification of the marking, in particular of the bar codes of the tubes (not shown in the figures), through the observation slits 8 takes place precisely at the sample-removal location. When a new rotor 1 is inserted, it is first of all rotated until a marking 11, which forms the zero position, is detected by the identification device. An "inventory" of all the tubes in the two outer, circular rows is then compiled in order thus to produce a defined relationship between an individual tube and its location in the rotor, with the result that, for renewed tests or any sequence of test, it is possible to advance quickly to a desired tube at any time. For emergency cases or other unplanned tests, it is possible for tubes to be inserted in the innermost row, although these tubes cannot be identified automatically.

FIG. 5 shows a second embodiment, in the case of which the reagent unit 4 is located in the centre between the two rotors 1. One of these rotors 1 is shown outside the apparatus. The gear wheel 9 and a protrusion 20 with a ball 19 loaded by a spring 25 can be seen in the recess into which the rotor can be pushed (see FIG. 6). At the front (at the location of the designation 14 on the left-hand rotor 1 in FIG. 5), the mount 14 has a recess which interacts with the protrusion 20 such that the mount 14 can only be inserted at the correct angle and is retained at an angle. The spring-loaded ball 19 then latches in the recess, with the result that the mount 14, and thus the rotor, can be secured simply, but reliably, in the apparatus and can easily be drawn out of the latter again.

As is shown from the side in FIGS. 9 and 10, the rotor 1 is inserted into the mount 14, which has a central spindle 12. In the embodiment shown in FIG. 7, the base 13 is pushed onto the central spindle 18 of the rotor beforehand, and said base can be arrested at different heights with the aid of a screw 15. The depression 17 in the central spindle 18 of the rotor is a rotation-prevention means and, at the same time, ensures that the screw 15 can always be adjusted through an observation slit, even following assembly. The resulting unit comprising rotor 1 and base 13 is positioned on the central spindle 12 of the mount 14. Finally, the rotor 1 is then secured on the central spindle 12 with the aid of a screw 16.

In the embodiment of FIG. 8, a screw rod 22, which can be rotated with the aid of a grip 21, is provided instead of the central spindle 18 of the embodiment of FIG. 7. This screw rod 22 interacts with a screw section 23 which is fastened on the base 13, which is arranged in a rotationally fixed manner. The height of the base 13 can then be adjusted by rotation of the grip 21. In this case, the grip 21, together with a further element 24, may serve as a mount for the insertion of the rotor into a centrifuge.

I claim:

1. Apparatus for analyzing body fluids which are contained in tubes provided with an externally readable identification marking, with positive sample identification at the position at which a quantity of fluid is removed for analysis and wherein the tubes are inserted into a rotatable rotor, comprising at least two rotors insertable into the apparatus in a sliding manner, the rotors each having observation slits arranged on its circumference for identification of the tubes and a laterally arranged gear wheel associated with each rotor for engaging the observation slits and driving the rotor.

2. Apparatus according to claim 1, wherein a marking is provided on the circumference of each rotor for reading as a reference position.

3. Apparatus according to claim 1, wherein the gear wheels are provided with a position sensor.

4. Apparatus according to claim 1 wherein the gear wheel idles along with the rotor as the rotor is pushed in/drawn out.

5. Apparatus according to claim 1 wherein each rotor includes two concentric rows of receiving openings for tubes being identified and a third row, which is arranged concentrically as an inner circle, for unplanned tests.

6. Apparatus according to claim 1 including a computer.

7. Apparatus according to claim 1, including means for connection to an external computer.

8. Apparatus according to claim 1 wherein the rotors have a vertically adjustable base.

9. Apparatus according to claim 8, including a screw accessible through one of the observation slits for arresting said adjustable base.

10. Apparatus according to claim 1, including mounts for the rotors having a flat front side, lateral centering surfaces which taper to the front, and a grip.

11. Apparatus according to claim 1, including mounts for the rotors having a semicircular front side and a recess in said front side, the apparatus further including a protrusion having a spring-loaded ball for angled securing of the mount.

12. Apparatus according to claim 1, including a base with a threaded section, a screw rod interacting with the threaded section for the purpose of vertical adjustment of the rotor, the screw rod having a grip for rotating the screw rod.

* * * * *